(12) United States Patent
Olschewski

(10) Patent No.: US 6,369,889 B1
(45) Date of Patent: Apr. 9, 2002

(54) METHOD AND DEVICES FOR CHECKING CONTAINER GLASS

(76) Inventor: Dieter Olschewski, Geilrather Weg 42, D50170 Kerpen (DE)

( * ) Notice: Subject to any disclaimer, the term of this patent is extended or adjusted under 35 U.S.C. 154(b) by 0 days.

(21) Appl. No.: 09/319,256

(22) PCT Filed: Dec. 9, 1997

(86) PCT No.: PCT/DE97/02873

§ 371 Date: Jun. 11, 1999

§ 102(e) Date: Jun. 11, 1999

(87) PCT Pub. No.: WO98/26278

PCT Pub. Date: Jun. 18, 1998

(51) Int. Cl.[7] .............................. G01N 21/00; G01N 9/04
(52) U.S. Cl. ............................. 356/239.4; 250/223 B
(58) Field of Search ..................... 356/239.1, 239.4, 356/239.5, 239.7, 240.1, 428; 250/223 B, 224; 209/526, 523, 524, 939

(56) References Cited

U.S. PATENT DOCUMENTS

| | | | | |
|---|---|---|---|---|
| 4,367,405 A | * | 1/1983 | Ford | 250/223 B |
| 4,376,951 A | * | 3/1983 | Miyazawa | 358/106 |
| 4,378,493 A | * | 3/1983 | Dorf et al. | 250/223 B |
| 4,584,469 A | * | 4/1986 | Lovalenti | 250/223 B |
| 4,586,080 A | | 4/1986 | Hoyt et al. | 358/106 |
| 4,694,158 A | * | 9/1987 | Leser | 250/223 B |
| 4,701,612 A | | 10/1987 | Sturgill | 250/223 B |
| 4,865,447 A | * | 9/1989 | Shay | 356/240 |
| 4,874,940 A | * | 10/1989 | McMeekin et al. | 250/223 B |
| 4,915,237 A | * | 4/1990 | Chang et al. | 209/524 |
| 4,975,568 A | * | 12/1990 | Taniguchi et al. | 250/223 B |
| 5,095,204 A | * | 3/1992 | Novini | 250/223 B |
| 5,200,801 A | * | 4/1993 | Juvinall et al. | 356/428 |
| 5,436,722 A | * | 7/1995 | Baldwin | 356/240 |
| 5,442,446 A | * | 8/1995 | Gerber et al. | 356/428 |
| 5,495,330 A | | 2/1996 | Champaneri et al. | 356/240 |

FOREIGN PATENT DOCUMENTS

| | | |
|---|---|---|
| EP | 0222959 | 5/1987 |
| EP | 0456910 | 11/1991 |
| GB | 2062855 | 5/1981 |
| GB | 2276447 | 9/1994 |
| WO | WO 8103706 | 12/1981 |

* cited by examiner

*Primary Examiner*—Frank G. Font
*Assistant Examiner*—Michael P. Stafira
(74) *Attorney, Agent, or Firm*—McDermott, Will & Emery

(57) ABSTRACT

A device for testing for cracks or irregularities in transparent or partially transparent containers uses a light source and optical reception device which outputs a signal which varies with the intensity of the impining light. The light source is powered by a clocked direct current.

21 Claims, 2 Drawing Sheets

METHOD AND DEVICES FOR CHECKING CONTAINER GLASS

BACKGROUND OF THE INVENTION

1. Field of the Invention

The present invention relates to a method and device for inspecting container glass or other transparent or partially transparent containers, and more specifically to a method and device which detect cracks or the like type of defects in such containers.

2. Related Art

In the production of glass used for containers, or in the production of other transparent or also partially transparent containers, quality assurance of the production process is one of the highest priorities. This is especially important in the case of jars for storing food and of glass containers intended for storing pharmaceutical products and while not being limited to aspects of product liability, does find important application in connection therewith.

In this connection, quality assurance has to ensure the absence of cracks in the containers.

The major part of quality assurance methods in current use are still based upon manual visual inspection. However, such inspection can be continuously conducted by people only for a short period of time, since considerable fatigue occurs rapidly usually leading to a drastic rise in the error rate. Inasmuch as this is intolerable for at least the above-mentioned mentioned reasons, frequent and extended breaks are necessary for the personnel involved, resulting in an increased need for manpower and attendant high costs.

Automatic methods for testing for cracks in containers have been previously proposed. These can, on one hand, be differentiated into methods which implement monitoring via the use of a camera for image generation and an accompanying method for evaluating the pictures/images using arrangements such as described in DE 195 38 013 A1 or also by DE 35 32 068 C2, EP 0 456 910 A1, U.S. Pat. Nos. 4,958,223 and 4,701,612. On the other hand, they can be differentiated into methods which use simple optical sensors monitor and rely only on the light intensity, such as described in the DE 35 24 943 A1.

The principal disadvantage of the picture evaluating methods and devices is the enormous amount of computational performance which is required to achieve a practical level of operation. It is imperative to ensure that the testing device does not slow down the output of the machine producing the containers. Consequently either very fast and therefore expensive evaluating computers, as those in highly parallel technology or a number of parallel testing devices are necessary. Both however, involve high costs.

The other approach which uses simple optical sensors which only monitor light intensity, is, in comparison, much easier to implement. Correspondingly, the necessary speed can be attained at a considerably lower cost, as compared with the above mentioned methods. An example of such a testing method and device therefore is described in the DE 35 24 943 A1.

This arrangement makes use of the fact that a light ray striking the posterior surface (interior wall) of a wall of a glass container is nearly reflected in its entirety. If the wall is free of any defect, a reflected light ray leaves the wall again at an angle of reflection equal to that of the angle of incidence. In the case wherein a crack runs through the container wall, the already reflected, exiting light ray is reflected again at the crack (or at an irregularity), and can be received by a suitably arranged detector as an error reflex/indication. Such a device is inexpensive with regard to its components and is furthermore suitable for operating with a very rapid and, in comparison to the picture evaluating methods, less expensive evaluating method.

A principal disadvantage to this, however, is the fact that such devices and the methods necessary for their operation have proven to be not always reliable. It is particularly difficult to adjust them with respect to the material of the container, which changes the angle of reflection. To this effect, blue glass reflects to a much lesser degree than white glass, and it is therefore a problem to reliably adjust a device with respect to the optical properties of the products being tested.

SUMMARY OF THE INVENTION

It is the object of the present invention to provide a method/arrangement of the nature disclosed in DE 35 24 943 A1, but which is so improved as to enable testing of transparent or partially transparent containers for cracks and other irregularities (defects) by means of simple optical sensors, wherein only the light intensity is monitored but which ensures adequate reliability and adjustment flexibility with respect to container material.

This problem is solved, according to the invention, by a device and a method for testing for cracks or irregularities (defects) of containers, wherein the device comprises means for moving the container, preferably to rotate, and an optical reception device which converts the light received into an electrical signal which varies in accordance with the intensity of the received light. In addition OT this reception and monitoring means are provided to receive the electrical signal over the time of the movement, and to monitor it with regard to whether the electrical signal exceeds a specific limit value. The device is characterized according to the invention in that the light source is powered by clocked direct current and in that the frequency of the clocked direct current can be adjusted. The method for testing for cracks or irregularities of containers comprises the following method steps:

(i) First, a container is moved, preferably rotated along its longitudinal axis.

(ii) A light ray of clocked constant light (light, which originates from a light source powered by clocked direct current) is directed upon the part of the moving, preferably rotating container.

(iii) A light ray reflected by the container is received by an optical reception device which is positioned in such a way that it lies in or about the focus or the focal level of a light ray which is typically reflected by a crack.

(iv) The optical reception device converts the received light into an electrical signal which changes according to the intensity thereof.

(v) The electrical signal is monitored during the movement of the container to determine if it exceeds a specific limit value.

Optionally the following steps could be subsequently taken:

(vi) If the limiting value is not exceeded during the container movement the examined container is marked as GOOD.

(vii) If the limiting value is exceeded during the movement the respective container tested is marked as POOR.

The clocked direct current referred to is a direct current which is cyclically switched on and off.

The frequency of the clocked direct current used for the operation of the lamp is adjustable with the device according to the invention in such a manner as to allow it to be adapted to the respective optical conditions/characteristics of the containers being inspected.

As a lamp a halogen lamp, possibly a H2 or H4 halogen lamp can be used.

The use of clocked constant light is advisable because measurements with alternating light (light originating from a source powered by alternating current) have proven that this is unsuitable for working of the method according to the invention and in contrast the suitability of clocked constant light was found to be surprisingly good. The frequency for clocking the light is thereby depend ant on the type of material, which may be transparent or semi-transparent material such as glass, from which the containers are made.

It has been shown that blue glass evokes a poorer quality of reflection in comparison to white (viz., water white) glass. The poorer the reflection of the glass (material), the higher the frequency of the light's clocking should be set. Good results were achieved with H4 halogen lamps at 20 kHz, which have proven to be also especially suited in the detection of cracks in containers made of blue, poorly reflecting glass.

The optical reception device can be embodied as a photo element, preferably as a photodiode.

A preferred embodiment according to the present invention is characterized by a picture reception device which can be used for the reception of a two-dimensional picture, such as a CCD chip.

The optical reception device is preferably mounted on a positioning device which makes it possible to position the optical reception device at different focal levels.

Between the optical reception device and the object to be tested, a lens system can be additionally provided.

By using of a picture reception device for the reception of a two-dimensional picture, such as a CCD chip, an especially clear focusing of the device can be achieved. Here, the picture reception device does not serve, as in the case of using picture evaluating methods for testing for cracks, to produce a complete two-dimensional picture for computer evaluation, but rather for focal adjustment of the system. The optical information received by the picture reception device is routed to a display device, such as a monitor screen. Here, the operator of the device can adjust the system to an optimal state by taking a defective object to be tested, namely one with a crack within the range of the reception area of the picture reception device, and positioning the same in such a way, for example by using the positioning device, that the light rays reflected by the crack lie within the focal level of the picture reception device.

This can be performed with ease when a monitor shows the picture received by the picture reception device thus enabling the operator to receive an optical feedback with respect to the selected adjustment. He/she positions the picture reception device in such a way that the crack can be clearly identified on the monitor. After this it is possible to determine which area of the two-dimensional picture received by the picture reception device, is to be converted with respect to its intensity into an electrical signal for further evaluation. The intensity measured in the selected area is subsequently processed. Thus, the intensity in the relevant area can be evaluated by summing the intensities of individual picture elements and determining a mean value, or the like.

A preferred embodiment of the method for testing for cracks of containers, according to the present invention is further characterized by the fact that the limit value to be monitored in step (v) of the above method is automatically evaluated (updated) starting from a freely (arbitrarily) selected initial value during the working of the method in that a measured maximum value for the reflected light intensity is chosen out of a certain amount of containers each during their movement (which, as noted above, is preferably a rotational movement) and is used as a new limit value for the further working of the method.

In a further embodiment of the method, only such measured maximum values are taken into the automatic evaluation of the limit value, which originate from containers marked as GOOD.

Preferably, the number of containers to be used in the automatic evaluation of the limit value, can be chosen freely.

A certain percentage exceeding of the respective limit value to be monitored is not yet treated as an exceeding of the limit value in a further embodiment for the further course of the method according to the present invention.

Preferably, the size of the percentage exceeding may also be selected freely, here.

A further preferred embodiment of the method according to the present invention here, is characterized by the fact that the signal received in step (iv) is amplified, preferably linearly amplified, before the further working of the method.

A further, particularly preferred embodiment of the method according to the invention is characterized by the fact that before its further processing (monitoring) in step (v), the signal, which is received in step (iv) and possibly already amplified, is first differentiated with respect to time in such a way that it is then no longer the signal or its amplification itself, but its differentiation with respect to time or the differentiation with respect to time of its amplification which is monitored with regard to a limit value. In this manner, a particularly good detection is assured, since cracks in the containers' material are for the major part, very fine and may occur in an abrupt way. Thus, the electrical signal according to the invention caused by the cracks changes rapidly at the crack edges. However, a rapid change of the signal also effects a particularly strong signal differentiated with respect to time, which is also to be detected quite effectively by means of threshold monitoring.

All in all, the present invention here guarantees a high level of reliability and flexibility in the detection of cracks, whereby it is particularly suitable for optically difficult objects to be tested, and therefore does not need any elaborate and thus cost-intensive picture evaluating methods including the required devices, such as highly parallel computers.

BRIEF DESCRIPTION OF THE DRAWINGS

Following is a description of non-restrictive embodiments, which are described further with regard to the drawing. This drawing shows.

DETAILED DESCRIPTION OF THE PREFERRED EMBODIMENTS

Figure 1:
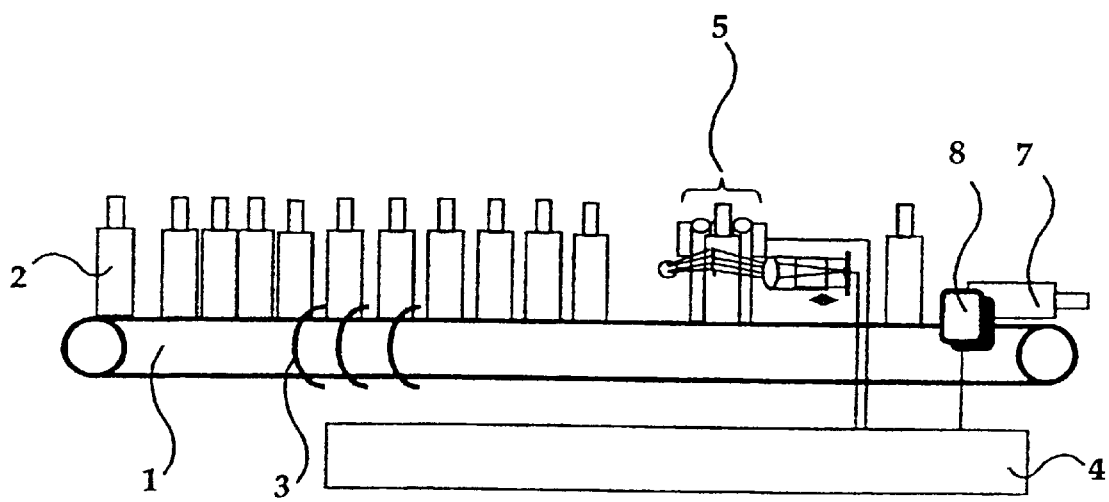
FIG. 1: An illustration, in a schematic side view, of a container testing arrangement in accordance with an embodiment of a testing device according to the present invention.

FIG. 1 illustrates, in schematic side view, a container testing arrangement according to an embodiment of the present invention. A conveyor belt 1 is used to convey glass containers 2, in this instance, bottles in a condition wherein they are initially spaced apart from each other at a defined distance by a spacing coil 3. A process computer 4 establishes the position of the bottles 2, which have been previously spaced at a defined distance by the spacing coil 3 and the current position of the conveyor belt 1 using a pulse generator or an angle encoder. In addition to this, light barriers, approach sensor switches or other suitable sensors may be used to receive, for example, absolute positional information for a specific bottle or as initial information. Alternatively, an absolute value generator may also be used.

At a certain position on the conveyor belt 1, an inspection or testing for cracks 5 according to the invention takes place. Further testing methods may be used, such as pressure-, shape- and rotational symmetry tests or also code recognition methods employing the necessary devices in combination with the device according the present invention. If the respectively tested (inspected) bottle passes the testing for cracks, then it is allocated an OK marker in the memory of the process computer 4 which serves as the process control device. If it fails the test, it is allocated a NOT-OK marker. At the end of the conveyor belt, those bottles 7 which do not fulfill a coded quality criterion may be selected out of the further production process via a blow-off device 8, whereas the bottles, which fulfill the set technical quality criterion remain in the further production process.

Figure 2:
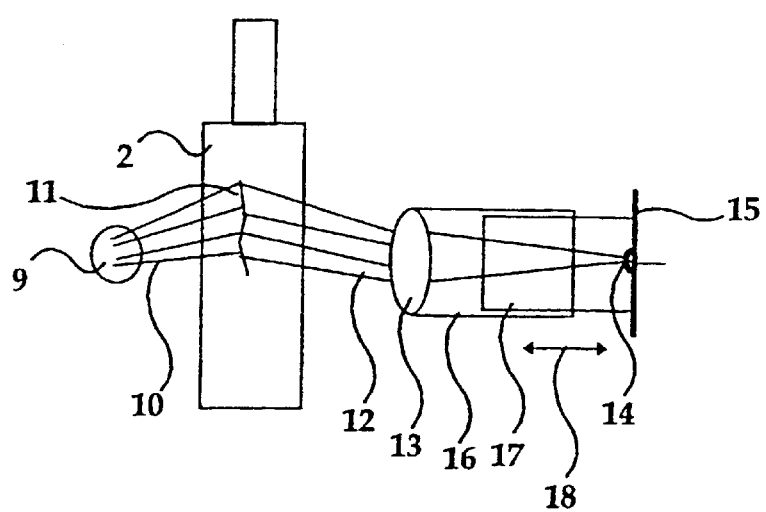
FIG. 2: an embodiment of a testing device according to the present invention, also illustrated in a schematic side view.

FIG. 2 illustrates a crack testing device according to the present invention, also illustrated in a schematic side view. From a light source 9 a light ray 10 is emitted, which is directed upon the section of the bottle 2 which is to be tested for cracks 11. The light ray 12 reflected by the crack 11 is focused by a lens 13 and is directed onto an optical reception device 14, preferably a photodiode, which is arranged on the lid surface 15 of a cylinder 17, and by means of two cylinders nesting within each other, 16 and 17, which are capable of being displaced towards each other along the directions of the arrows 18, and thus serving as a positioning device, is adjusted with regard to the focal level of the focused light ray, whereby this has to take place in such a way that the optical reception device 14 is positioned in such a way that it lies approximately in the focus or focal level of the light ray, which is reflected by the crack 11 and the preferably further focused light ray. The photo element 14 converts the light received into an electrical signal which is then processed. The light rays reflected by the cracks 11 are typically reflected in such a way that the photo element 14 is adjusted to a distance, which is determined once of the lens 13, whereupon all the light rays 12 reflected by the cracks 11 after being focused by the lens 13, have approximately their focus at the location of the photo element 14, which enables an accurate detection of cracks by the device.

Figure 3:
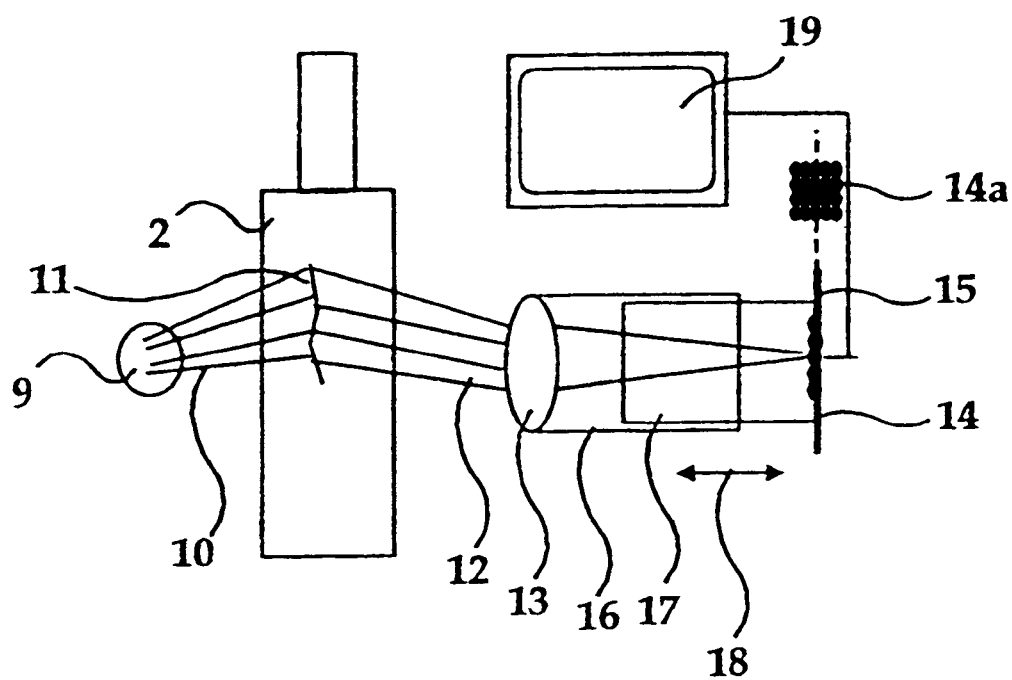
FIG. 3: a further particularly preferred embodiment of a testing device according to the present invention again illustrated in a schematic side view.

FIG. 3 illustrates a further particularly preferred embodiment of a testing device according to the present invention, likewise illustrated in a schematic side view. From a light source 9 a light ray 10 is emitted, which is directed upon the section of the bottle 2 to be tested for cracks 11. The light ray 12 reflected by the crack 11 is focused by a lens 13 and is directed onto an optical reception device 14, which is namely a two-dimensional picture reception device (also in the top view referred to as 14*a*), preferably a CCD matrix (CCD chip or also a Charged Coupled Device component), which is arranged on the lid surface 15 of a cylinder 17 and by means of two cylinders nesting within each other, 16 and 17, which are capable of being displaced towards each other along the directions of the arrows 18 and can thus serve as a positioning device, is adjusted with regard to the focal level of the focused light ray, whereby this has to take place in such a way that the optical reception device 14 is positioned in such a way that it lies approximately in the focus or focal level of the light ray which is reflected by the crack 11 and the preferably further focused light ray. By using a picture reception device 14, 14*a* for the reception of a two-dimensional picture, preferably a CCD chip, an especially clear focusing of the device can be achieved. The optical information received by the picture reception device 14, 14*a* is then routed to a display device 19, preferably a monitor screen. Here, the operator of the device can adjust the system as follows in an optimal manner: He takes a defective object 2 to be tested, namely one with a crack 11 within the range of the reception area of the picture reception device 14, 14*a* and positions the same, for example, by using the positioning device 16, 17 in such a way that the light rays 12 reflected by the crack 11 lie within the focal level of the picture reception device 14, 14*a*. This can be performed with ease as the monitor 19 reproduces the picture received by the picture reception device 14, 14*a* giving the operator an optical feedback about the quality of the selected adjustment. He has to position the picture reception device 14, 14*a* in such a way that the crack 11 can be clearly identified on the monitor. After this he can preferably determine which area of the two-dimensional picture received by the picture reception device 14, 14*a* intended as an optical reception device according to die present invention, with regard to its intensity, is to be converted into an electrical signal for further evaluation. This can be achieved by, possibly, selecting one of the sections of the picture displayed on the monitor 19. The light received within this selected area is then converted into an electrical signal which is then further processed. Thereby, a particularly secure detection of cracks is made possible by the device according to the invention.

What is claimed is:

1. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and varying a frequency of the clocked direct current in accordance with a predetermined operational parameter.

2. A method as set forth in claim 1, wherein the predetermined operational parameter is the material from which the container is made.

3. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value; and determining the presence of a defect based on the comparison of the signal and the predetermined value; wherein the step of arranging the optical receptor device includes the steps of:

using a CCD device as the optical receptor;

mounting the CCD device on a positioning device;

disposing a bottle having a predetermined defect such as a crack or irregularity, on the conveyor arrangement; and using an image produced by the CCD device to adjust the positioning device to move the CCD device to a position wherein light, which is reflected by the defect is suitably received by the CCD device and wherein the signal indicative of the received light intensity can be generated.

4. A method as set forth in claim 1, wherein the predetermined movement is rotation of the container about a longitudinal axis thereof.

5. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and indicating that the container is GOOD in the event that the step of determining the presence of a defect indicates that the signal intensity is lower than the predetermined value.

6. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and indicating that the container is POOR in the event that the step of determining the presence of a defect indicates that the signal intensity is equal to or greater than the predetermined value.

7. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and automatically evaluating the predetermined value during container testing by:

starting with a given value;

testing a plurality of containers and determining a plurality of signal values;

selecting a maximum signal value from among a selected plurality of signal values which indicate that the container is free of defects; and resetting the given value as the predetermined value based on the selected maximum signal value.

8. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and wherein the predetermined value is automatically evaluated after starting from an arbitrarily selected initial value and then testing a plurality of containers, and wherein a maximum value of the signals generated during the testing of the plurality of containers is used as a new predetermined value.

9. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and wherein the predetermined limit must be exceeded by a predetermined percentage of the predetermined value before the presence of a defect is determined to be present.

10. A method of testing a container for defects comprising the steps of:

moving the container in a predetermined manner;

directing a beam of light, which is produced by a light source, at the container for at least a period sufficient to allow a predetermined amount of movement of the container;

arranging an optical receptor device at a location to which the defects in the container direct the beam of light from the light source;

energizing the light source with a clocked direct current;

converting the light received by the optical receptor device into a signal indicative of the received light intensity;

comparing the signal with a predetermined value;

determining the presence of a defect based on the comparison of the signal and the predetermined value; and differentiating the signal indicative of the intensity of the received light with respect to time before the comparison with the predetermined value.

11. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value;

means for determining the presence of a defect based on the comparison of the signal and the predetermined value; and means for varying a frequency of the clocked direct current in accordance with a predetermined operational parameter.

12. An apparatus as set forth in claim 11, wherein the predetermined operational parameter is the material from which the container is made.

13. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; wherein the means for arranging the optical receptor device includes:

a CCD device as the optical receptor, the CCD device being mounted on a positioning device; and a monitor which displays an image generated by the CCD device and which is used to adjust the position of the CCD device by using a bottle having a defect and using an image appearing on the monitor to adjust the positioning device to move the CDD device to a position where light, which is reflected by the defect is suitably received by the CDD device and wherein the signal indicative of the received light intensity is generated.

14. An apparatus as set forth in claim 11, wherein the predetermined movement produced by the moving means is rotation of the container about a longitudinal axis thereof.

15. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; and means for indicating that the container is GOOD in the event that the comparing means indicates that the signal intensity is lower than the predetermined value.

16. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; and means for indicating that the container is POOR in the event that comparing means indicates that the signal intensity is equal to or greater than the predetermined value.

17. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value;

means for determining the presence of a defect based on the comparison of the signal and the predetermined value; and means for automatically evaluating the predetermined value during container testing by:
  starting with a given value;
  testing a plurality of containers and determining a plurality of signal values;
  selecting a maximum signal value from among a selected plurality of signal values which indicate that the container is free of defects; and
  resetting the given value as the predetermined value based on the selected maximum signal value.

18. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; and means for automatically evaluating the predetermined value by starting from an arbitrarily selected initial value and then testing a plurality of containers, and wherein a maximum value of the signals generated during the testing of the plurality of containers, is used as a new predetermined value.

19. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; and wherein the means for determining the presence of a defect is set to that the predetermined value must be exceeded by a predetermined percentage of the predetermined value before the presence of a defect is determined to be present.

20. An apparatus for testing a container for defects comprising:

means for moving the container in a predetermined manner;

means for directing a beam of light, which is produced by a light source, at the container for at least a period sufficient to allow a predetermined amount of movement of the container;

means for supporting an optical receptor device at a location to which a defect in the container direct the beam of light from the light source;

means for energizing the light source with a clocked direct current;

means for converting the light received by the optical receptor device into a signal indicative of the received light intensity;

means for comparing the signal with a predetermined value; and means for determining the presence of a defect based on the comparison of the signal and the predetermined value; and means for differentiating the signal indicative of the intensity of the received light with respect to time before comparison with the predetermined value in the comparing means.

21. An apparatus for testing a container for defects comprising:

a conveyor arrangement which moves the container in a predetermined manner;

a light source which directs a beam of light at the container for at least a period of time sufficient to allow a predetermined amount of movement of the container, the light source being energized by a source of clocked direct current;

an optical receptor device disposed at a location to which a defect in the container directs the beam of light from the light source, the optical receptor device converting the light received by the optical receptor device into a signal indicative of the received light intensity; and a circuit which compares the signal with a predetermined value and determines the presence of defects based on the comparison; wherein the circuit differentiates the signal indicative of the intensity of the received light with respect to time before comparison with the predetermined value.

* * * * *